(12) United States Patent
Sakuth et al.

(10) Patent No.: US 6,881,699 B1
(45) Date of Patent: Apr. 19, 2005

(54) METHOD FOR PRODUCING A DEALUMINIZED CATALYST SUPPORT

(75) Inventors: Michael Sakuth, Marl (DE); Gregor Lohrengel, Dorsten (DE); Dietrich Maschmeyer, Recklinghausen (DE); Guido Stochniol, Marl (DE)

(73) Assignee: Sasol Germany GmbH, Hamburg (DE)

( * ) Notice: Subject to any disclaimer, the term of this patent is extended or adjusted under 35 U.S.C. 154(b) by 0 days.

(21) Appl. No.: 09/701,054

(22) PCT Filed: Jul. 1, 1999

(86) PCT No.: PCT/DE99/01898

§ 371 (c)(1),
(2), (4) Date: Feb. 8, 2001

(87) PCT Pub. No.: WO00/01480

PCT Pub. Date: Jan. 13, 2000

(30) Foreign Application Priority Data

Jul. 3, 1998 (DE) .......................... 198 29 747

(51) Int. Cl.[7] ............................................. B01J 27/182
(52) U.S. Cl. .................. 502/214; 502/263; 502/439
(58) Field of Search ................. 502/214, 232, 502/240, 263, 80, 81, 83, 85, 439

(56) References Cited

U.S. PATENT DOCUMENTS

| 2,579,601 A | | 12/1951 | Nelson et al. | |
| 3,311,568 A | | 3/1967 | Klimenko | |
| 4,299,730 A | | 11/1981 | Sommer et al. | |
| 4,581,215 A | * | 4/1986 | Kaeding | ................... 423/715 |
| 4,696,732 A | * | 9/1987 | Angevine et al. | ....... 201/111.15 |
| 4,714,537 A | * | 12/1987 | Jorgensen et al. | ...... 201/111.15 |
| 4,808,559 A | | 2/1989 | Sommer et al. | |
| 4,919,790 A | * | 4/1990 | Absil et al. | .................... 208/78 |
| 4,967,020 A | | 10/1990 | Marler et al. | |
| 5,080,778 A | * | 1/1992 | Lambert | ................ 208/111.15 |
| 5,145,659 A | * | 9/1992 | McWilliams | ................ 423/713 |
| 5,208,195 A | * | 5/1993 | Schlueter et al. | ............. 502/63 |
| 5,248,841 A | * | 9/1993 | Young | ........................ 585/467 |

FOREIGN PATENT DOCUMENTS

| EP | 0578441 | 10/1987 |
| EP | WO 99/022860 | 8/2000 |
| GB | 981237 | 1/1965 |
| GB | 1306141 | 2/1973 |

* cited by examiner

*Primary Examiner*—Stanley S. Silverman
*Assistant Examiner*—Edward M. Johnson
(74) *Attorney, Agent, or Firm*—C. James Bushman; Browning Bushman P.C.

(57) ABSTRACT

What is claimed is a dealuminated catalyst carrier, a process for producing a catalyst carrier with reduced aluminum content based on naturally occurring lattice-layer silicates, such as, for example, montmorillonite, as well as a process for the hydration reaction of $C_2$- or $C_3$-olefins in which said catalyst carrier with reduced aluminium content is used. For acid-catalysed hydration reaction the catalyst carrier is impregnated with phosphoric acid. The improvements according to the invention of the hydration reaction compared to conventional processes include the fact that no aluminium is leached out of the carrier in the presence of the phosphoric acid. As a result no more blockage of the succeeding apparatus due to aluminium phosphate is expected.

10 Claims, 1 Drawing Sheet

METHOD FOR PRODUCING A DEALUMINIZED CATALYST SUPPORT

Dealuminated catalyst carrier, process for producing the catalyst carrier and process for hydrating $C_2$ or $C_3$ olefins with water in the presence of a catalyst which consists this catalyst carrier impregnated with acid.

BACKGROUND OF THE INVENTION

1. Field of the Invention

Claimed is a dealuminated catalyst carrier, a process for producing the catalyst carrier and a process for hydrating $C_2$- or $C_3$-olefins with water in the presence of a catalyst which comprises this catalyst carrier impregnated with acid.

2. Description of the Prior Art

It is known that olefins of low molecular mass which are linear or have only few branches can be converted to alcohols by a reaction with steam in the gas phase under the application of high temperatures and pressures. Of significance for large scale is the synthesis of ethanol from ethene and of isopropanol from propane. The production of these alcohols takes places in the presence of acidic catalysts, wherein usually a catalyst carrier consisting of an alumosilicate and a silicate material is used, which has been impregnated with phosphoric acid, respectively.

The material of the catalyst carrier is usually made up of pure silicic acid, such as, for example, silica gel (U.S. Pat. No. 2,579,601) or consists of silicic acid with a varying amount of alumina (U.S. Pat. No. 3,311,568) and consists of pure lattice-layer silicates (sheet-structure silicates), such as, for example, those containing montmorillonite (DE 29 09 491), respectively.

Apart from these phosphoric acid-containing catalyst carriers, also zeolithic materials are used (EP 0 323 269 B1) or other acidic catalysts, such as, for example, zircon phosphate (GB 00 55 34).

Until now, for carriers that are based exclusively on silicic acid in the form of silica gel, the mechanical hardness is questionable over a longer period of time. Aluminium/containing catalyst carriers or those consisting of only alumina show a noticeably higher long-term stability, but they have the immense disadvantage that aluminium is leached out from the catalyst carrier during the hydration reaction due to the effect of phosphoric acid. The aluminium ends up in the succeeding apparatuses as poorly soluble sedimentations in form of aluminium phosphate. These apparatuses thus are gradually blocked.

In DE 1 156 772 a process is described for reducing the aluminium content of the lattice-layer silicate by reaction with hydrochloric acid. However, even after intensive washing with hydrochloric acid, the carrier material still shows the presence of approximately 1 to 2% by weight of aluminium.

In EP 0 578 441 B1 by using a pelletised silicate carrier based on aerosil (Degussa) which does not contain aluminium, a certain long-term stability is achieved. Starting material for the production of aerosil is the relatively expensive silicon tetrachloride. Since materials based on lattice-layer silicates, such as montmorillonite, for example, are natural raw materials which can be excavated from relevant deposits in the earth, these have an obvious advantage over pelletised silicate carriers according to the economic efficiency of the hydrating process.

SUMMARY OF THE INVENTION

Figure 1:
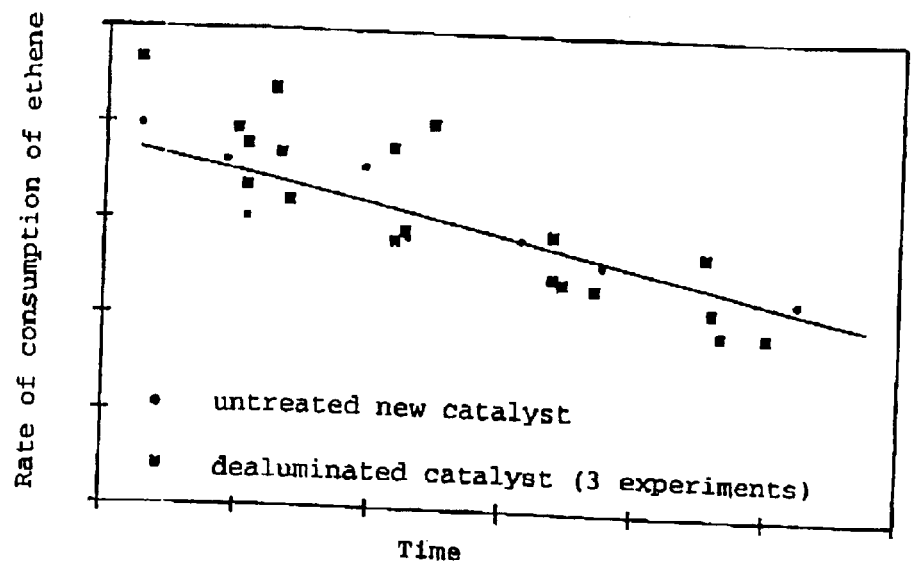
FIG. 1 is a graph showing the rate of consumption of ethene versus reaction time using differently treated catalyst carriers.

The present invention is based on the problem of finding an economical process for the hydration of $C_2$- and $C_3$-olefins with water in the presence of a catalyst which comprises a catalyst carrier impregnated with acid and in which the catalyst carrier has a long term stability as high as possible and simultaneously the leaching out of aluminium during the hydration reaction is as little as possible.

Surprisingly, it has been found that a dealuminated catalyst carrier based on mainly aluminium-containing lattice-layer silicates with a montmorillonite structure, and an aluminium content of less than 0.3% by weight has a high long-term stability, and that during the process of hydrating $C_2$- and $C_3$-olefins with water in the presence of a catalyst which comprises a catalyst carrier impregnated with acid, by carrying out the hydration reaction using a dealuminated catalyst carrier according to the present invention, no or only very small amounts of aluminium are washed out of the catalyst carrier.

An object of the present invention is therefore a dealuminated catalyst carrier based on mainly aluminium-containing lattice-layer silicates with a montmorillonite structure with an aluminium content of less than 0.3% by weight. Preferred forms of the catalyst and of the process are described in the sub-claims.

A further object of the present invention is a process for the reduction of the aluminium content of a catalyst carrier which comprises mainly aluminium-containing lattice-layer silicates with a montmorillonite structure, wherein the catalyst carrier is

- impregnated with phosphoric acid
- treated hydrothermally at a temperature of between 160 and 300° C. and a partial water vapour pressure of 4 to 80 $bar_{absolute}$
- washed subsequently with an acidic, basic or neutral solution at a temperature of between 20 and 100° C., and
- afterwards rinsed with water until the washing water becomes neutral.

Yet another object of the present invention is a process for the hydration of $C_2$- or $C_3$-olefins with water in the presence of a catalyst that comprises a catalyst carrier impregnated with acid according to the present invention.

DESCRIPTION OF THE PREFERRED EMBODIMENTS

The terms "hydration" and "hydration reaction" refer, for the purposes of this invention, to the reaction of water with a carbon—carbon double bond.

The terms "dealuminating" and "dealuminated catalyst carrier", respectively, refer for the purposes of this invention to the process of reducing the aluminium content and a catalyst carrier with a reduced aluminium content.

By carrying out the process according to the present invention, a catalyst carrier can be produced which is based on calcined and subsequently treated lattice-layer silicates and, that has a noticeably reduced aluminium content compared to a catalyst carrier that has not been treated according to this invention. In spite of the reduced aluminium content, the long-term stability of the catalyst has been maintained. By using a catalyst carrier according to this invention during the process also according to this invention for the hydration of $C_2$- or $C_3$-olefins olefins with water, the amount of aluminium leaching out during the hydration reaction is noticeably reduced. Thus, fewer insoluble aluminium compounds are produced during the hydration reaction, which in conventional processes lower the hold up time of the succeeding apparatuses, such as heat exchangers, by blocking the pipes or the areas of heat exchange.

The dealuminized catalyst carrier according to this invention with an aluminium content of less than 0.3% by weight contains mainly aluminium-containing lattice-layer silicates. In particular, a preferred dealuminized catalyst carrier according to this invention has an aluminium content of less than 0.03% by weight. The aluminium-containing lattice-layer silicates are preferably smectites and have preferably montmorillonite structures. Lattice-layer silicates which exhibit mainly aluminium-containing lattice-layer silicates with montmorillonite structures are, for example, the bentonites. Apart from the montmorillonites, bentonites can contain other components, such as, for example, mica, illite, crystobalite and zeolite.

Starting material for the production of a catalyst carrier according to the present invention are conventional catalyst carriers for examples based on calcined and subsequently treated lattice-layer silicates.

The dealuminized catalyst carrier according to this invention with an aluminium content of less than 0.3% by weight, preferably less than 0.03% by weight, based on mainly aluminium rich lattice-layer silicates with a montmorillonite structure can be made by impregnating the catalyst carrier with phosphoric acid, preferably a 10 to 90% by weight phosphoric acid, more particularly a phosphoric acid of 50 to 60% by weight so that the catalyst carrier contains between 5 and 60%, preferably between 30 and 40% phosphoric acid, followed by hydrothermal treatment at a temperature of between 160 and 300° C., preferably at a temperature of between 220 and 260° C. and a partial water vapour pressure of between 4 and 80 $bar_{absolute}$, preferably at a partial water vapour pressure of between 16 and 25 $bar_{absolute}$, followed by washing with an acidic, basic or neutral solution, preferably an acidic or neutral solution, in particular with water, hydrochloric acid or water containing 0 to 30 parts concentrated hydrochloric acid at a temperature of between 20 and 100° C., preferably of between 70 and 90° C. and afterwards rinsing the catalyst carrier until the washing water has become neutral.

An example of how to carry out the process according to the present invention for reducing the aluminium content of a catalyst carrier is described below, without limiting the process of the present invention to this example.

For the reduction of the aluminium content of a catalyst carrier which comprises mostly aluminium-containing lattice-layer silicates, commercial lattice-layer silicates such as, for example, montmorillonite or bentonite containing catalyst carriers, can be used. The catalyst carriers have preferably the form of spherical shapes, such as, for example balls, lenses, cuboids, cylinders or also irregular forms, in particular preferred they have the shape of balls. The spherical shapes have preferably an average diameter of 1 to 10 mm, most a preferably diameter of 4 to 6 mm.

For the reduction of the aluminium content in the catalyst carrier, it is impregnated with acid, treated hydrothermally, subsequently washed and afterwards rinsed.

The catalyst carrier is impregnated with acid, preferably phosphoric acid, in order to produce the effect according to the invention. A 10 to 90% by weight phosphoric acid, preferably a 50 to 60% by weight phosphoric acid, is used. After being impregnated, the catalyst carrier should show an amount of phosphoric acid of 5 to 60% by weight, preferably 30 to 40% by weight. Afterwards the catalyst carrier is treated hydrothermally.

Under the hydrothermal conditions the lattice-layer silicate material, such as, for example, montmorillonite changes into cristobalite-like structures. Accordingly the nicropores that were previously present disappear. These morphological changes in structure can clearly be seen by the BET surface, the pore volume and the distribution of pore radii. Under hydrothermal reaction conditions the so-called "open" pore structures are attained.

Hydrothermal treatment of the catalyst carrier containing lattice-layer silicates can be carried out at temperatures of between 160 and 300° C. under a partial water vapour pressure of between 4 and 80 $bar_{absolute}$, preferably between 220 and 260° C. and a partial water vapour pressure of between 16 and 25 $bar_{absolute}$.

After hydrothermal treatment the catalyst carrier is washed with a basic, acidic or neutral solution, preferably with an acidic or neutral solution, most preferably with hydrochloric acid, with water containing 0 to 30 parts concentrated hydrochloric acid or with a neutral aqueous solution. The washing of the catalyst carrier is carried out at a temperature of between 20 and 100° C., preferably between 70 and 90° C.

After said washing the catalyst carrier can be rinsed with water until the washing water used to rinse becomes neutral.

The catalyst carrier then has a cumulated pore volume of between 0.2 and 0.9 ml/g, preferably between 0.6 and 0.7 ml/g. The pressure resistance of the catalyst carrier should be of at least 10 N/mm, preferably at least 20 N/mm.

In a specific embodiment of the process according to the invention, the hydrothermal treatment of the catalyst carrier impregnated with acid, which contains 5 to 60% by weight phosphoric acid, preferably 30 to 40% by weight, takes place by use as a catalyst in a hydration reaction of $C_2$- or $C_3$-olefins. For impregnating the catalyst carrier, preferably a 10 to 90% by weight, most preferably a 30 to 60% by weight, phosphoric acid is used.

During this hydration in a reactor filled with catalyst, preferably a tubular reactor olefin and water in a molar ratio of between 0.1 and 0.0, preferably between 0.15 and 0.5, are reacted. The olefin to be used and the water to be used are introduced into the reactor gaseous or liquid, preferably gaseous. For evaporating the water and heating both reagents to reaction temperature, respectively, it may be beneficial to introduce both reagents into the reactor over a vaporisation or thermostat-controlled section, which is heated to the reaction temperature electrically or by way of heat carriers which lead into the reactor. The gas hourly space velocity (GHSV) should be between 10 and 100 $l_n/min/l_{cat}$. The hydration reaction is carried out at a temperature of between 160 and 300° C. and an absolute pressure of between 20 and 200 bar. The hydration of ethene to ethanol is carried out preferably at a temperature of between 220 and 260° C. and an absolute pressure of between 60 and 80 bar.

The exit of the reactor can preferably be connected to a cooler which condenses out the majority of the sub-critical components and makes them accessible to further reprocessing, such as, for example, distillative separation.

For controlling the activity and selectivity of the catalyst carrier impregnated with acid, it can be advantageous to analyse the outflow of the reactor. The analysis can be carried out by gas chromatography.

To increase the lifetime of the catalyst, it is advantageous to add the acid, with which the catalyst carrier has been impregnated, into the reactor continuously or discontinuously, preferably continuously. The acid can be introduced into the reactor, such as, for example, by injection. The amount of acid which is introduced into the reactor can be made dependent on the results of the analysis of the outflow. Both the analysis of the aforementioned energy released from the reaction, as well as the resulting amount of acid to be introduced can be carried out by automation.

After the hydrothermal treatment of the catalyst carrier by being used as a catalyst in a hydration reaction, the remaining acid with which the catalyst carrier has been impregnated is removed by washing with water until the washing water becomes neutral.

After the removal of the remaining acid, the catalyst carrier is washed with a basic, acidic or neutral solution preferably with an acidic or neutral solution and most preferably preferably with hydrochloric acid, with water which contains 0 to 30 parts concentrated hydrochloric acid or a neutral aqueous solution. The catalyst carrier can be washed at a temperature of between 20 arid 100° C., preferably at a temperature of between 70 arid 90° C.

After the washing the catalyst carrier can be rinsed with water until the washing water becomes neutral.

In the case of catalyst carriers which by being used as catalysts in a hydration reaction have been hydrothermally treated, it may be advantageous, after reducing the aluminium content in the catalyst carrier, to clean the catalyst carrier by burning off possible carbon compounds attached at between 300 and 1,000° C., preferably between 450 and 500° C.

Both variations of the process according to this invention result in a treated catalyst carrier with a reduced aluminium content. The treated catalyst carriers have an average diameter of between 1 and 10 mm, more preferably of between 4 and 6 min. The total pore volume is between 0.2 and 0.9 ml/g, preferably between 0.6 and 0.7 ml/g. The pressure resistance after the treatment of the catalyst carrier is at least 10 N/mm, preferably 20 N/mm. The amount of aluminium in the treated catalyst carriers is less than 0.3% by weight, preferably less than 0.03% by weight.

The catalyst carriers produced by the process according to this invention with reduced aluminium content can be used for the production of catalysts.

The catalyst carriers produced by the process according to this invention with a reduced aluminium content can according to the invention be used for the hydration of $C_2$- or $C_3$-olefins with water in the presence of a catalyst, which consists mainly of a catalyst carrier treated according to the invention having been impregnated with acid.

Preferably the catalyst carrier is impregnated with an acid, most preferably phosphoric acid. The quantity of phosphoric acid should be between 5 and 60% by weight, preferably between 30 and 40% by weight, to obtain the maximum catalytic activity of the impregnated catalyst carrier. For impregnating the catalyst carrier, an aqueous phosphoric acid solution which contains a phosphoric acid quantity of between 10 to 90% by weight, preferably between 50 and 60% by weighs is used. The acidic catalyst thus produced is filled in a reactor, preferably a tubular reactor. The reactor is operated isothermally or non-isothermally, preferably isothermally, and can be heated electronically or by way of heat carriers.

The reactor is fed continuously or discontinuously, preferably continuously, with the reagents water and $C_2$- or $C_3$-olefin. The ratio of water to olefin with which the reagents are fed into the reactor is adjusted at a molar ratio of between 0.1 to 0.8, preferably between 0.15 and 0.5. The molar ratio can be adjusted by, using for example a mass flowmeter. Both reagents can be introduced into the reactor liquid or gaseous, preferably gaseous. For evaporating the water and heating both reagents to reaction temperature, respectively, it may be beneficial to introduce both reagents into the reactor over a vaporisation or thermostat-controlled section, which is heated to the reaction temperature electrically or by way of heat carriers. The temperature in the reactor and the temperature with which the reagents flow into the reactor should be between 160 and 300° C.

For the hydration reaction of ethene to ethanol, the temperature in the reactor and the temperature with which the reagents flow into the reactor is preferably between 220 and 260° C. The pressure in the reactor is in the range of between 20 and 200 $bar_{absolute}$, preferably between 60 and 80 $bar_{absolute}$.

The exit of the reactor is preferably connected to a cooler, which can condense out the majority of the components and make these accessible to further reprocessing.

To control the activity and selectivity of the acid impregnated catalyst carrier, it can be beneficial to analyse the outflow of the reactor. This analysis can be carried out, such as, for example, by gas chromatography.

To increase the lifetime of the catalyst, it is advantageous to add the acid, preferably phosphoric acid, with which the catalyst carrier has been impregnated, into the reactor continuously or discontinuously, preferably continuously. The acid can be introduced into the reactor, such as, for example by injection. The amount of acid which is introduced into the reactor can be made dependent on the results of the analysis of the outflow. Both the analysis of the outflow and the determination resulting amount of acid to be introduced can be carried out by automation.

In FIG. 1 the rate of consumption of ethene during a hydration reaction is shown in dependence of the reaction time. The data from four experiments are shown. The measurements represented by circles refer to the rate of consumption of ethene relative to reaction time when a new catalyst carrier containing the original amount of aluminium is used. The data of the rate of consumption of ethene represented by squares result from three series of experiments which were carried out using a catalyst carrier with a reduced aluminium content.

Figure 2:
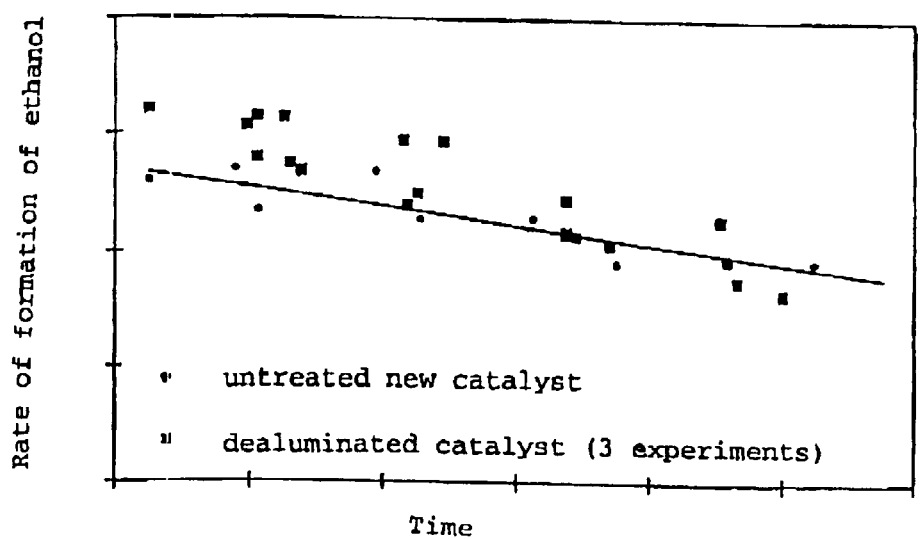
FIG. 2 is a graph showing the rate of consumption of ethanol versus reaction time using differently treated catalyst carriers.

In FIG. 2 the rate of formation of ethanol during in a hydration reaction in dependence of the reaction time is shown. The data from four experiments are shown. The measurements represented by circles refer to the rate of formation of ethanol relative to reaction time when a new catalyst carrier containing the original amount of aluminium is used. The data of the rate of formation of ethanol represented by squares refer result from three series of experiments which were carried out using a catalyst carrier with a reduced aluminium content.

The process according to the present invention is described by the examples below without being limited to these examples.

EXAMPLE 1

The Synthesis of Ethanol with an Untreated Catalyst Carrier

The experiment took place in a pilot plant whose core part contains an isothermally operated tubular reactor of 1,000 mm in length and 48 mm diameter.

The reagents water and ethene are introduced into the reactor over a vaporisation or thermostat-controlled section, which is electrically heated to the reaction temperature. The water is introduced liquidly through a pump, while ethene is taken from a 130 bar steel flask. The introduction of a mixture of ethene:water at a molar ratio of 0.3:1 is controlled by a mass flow-meter.

The exit of the reactor is connected to a cooler which condenses out the majority of the subcritical components, mainly ethanol, water and diethylether, the rest being diverted to the waste gas whose volumetric flow is measured by a gas-meter. A part of the waste gas is fed through a bypass into a gas chromatograph. The liquid products are also analysed by gas chromatography.

The synthesis of ethanol according to the present example was measured at a temperature of 240° C. and a pressure of 70 $bar_{absolute}$. The standard test conditions are summarised in Table 1. The catalyst used was an untreated new catalyst carrier, the KA-1 of Südchemie AG. The properties of the carrier are summarised in Table 2: Conversion and selectivity values reached at the start of the experiment are included in Table 2.

To determine the aluminium content of the catalyst carrier this was analysed with an atomic emission spectrometer before the start of an experiment. The atomic emission spectrometer used was an inductively coupled plasma atomic emission spectrometer (ICP-AES) JY 38+ made by ISA Jobin Y. The results of the analysis are shown in Table 2.

EXAMPLE 2

The Synthesis of Ethanol with an Untreated Old Carrier

The experiment was repeated in the same way as described in Example 1. This time an untreated catalyst carrier that had already been used for the catalysis of a hydration reaction is employed ('old carrier'). Again the standard test conditions shown in Table 1 are relevant. The results of the experiment as well as the properties of the catalyst carrier are given in Table 2.

As can be seen from the values in Table 2, the specific surface of the impregnated catalyst carrier decreases after the catalyst has been used only once. Similarly the aluminium content is reduced to approximately ¼ of its original value by the single use as catalyst. The remaining ¾ of the original amount of aluminium in the untreated new carrier are leached out during the hydration reaction. This aluminium forms the insoluble sedimentations which hinders the reprocessing steps.

EXAMPLE 3

The Synthesis of Ethanol with a Treated Old Carrier

The experiment was carried out in the same way as described in Example 1. As catalyst carrier an already used old carrier was employed whose aluminium content had been reduced by treatment according to the process of this invention. Again the standard test conditions shown in Table 1 are relevant. The results of the experiment as well as the properties of the catalyst carrier ire also given in Table 2.

The deactivation of the catalyst carrier with, as well as without, a reduced aluminium content are represented in both FIG. 1 and FIG. 2.

As can be seen from Table 2 the aluminium content of a catalyst carrier is reduced to less than 0.03% by weight by treating the old carrier in the process according to this invention. This value represents the detection limit of the atomic emission spectrometer used. The pressure resistance of the treated old carrier is 30 N/mm sufficient to guarantee good long-term stability of the catalyst carrier.

In spite of treating the catalyst carrier and reducing its aluminium content to a value less than 0.03% by weight, the conversion of ethylene and the yield of ethanol both remained good compared to an untreated, unused catalyst carrier ('new carrier') and to an untreated old carrier, respectively, even slightly increased in the present example.

As can be seen from FIG. 1 and FIG. 2 reducing the aluminium content according to the process of the invention has no influence on the rate of consumption of ethene nor on the rate of formation of ethanol.

TABLE 1

The standard experimental conditions used in all experiments.

Standard experimental conditions

| Process Parameter | Value |
| --- | --- |
| total reaction pressure | 70 bar |
| temperature of the reactor (isotherm) | 240° C. |
| GHSV | 21.3 $l_n/min/l_{cat}$ |
| water:ethene | 1.0:0.3 mol:mol |
| carrier material | KA-1 (Südchemie) |

TABLE 2

A comparison of the properties of the three types of catalyst carriers used

| Property (impregnated carrier) | New Carrier | Untreated Old Carrier | Treated Old Carrier |
| --- | --- | --- | --- |
| force withstood | 20 N/mm | 40 N/mm | 30 N/mm |
| spec. surface (BET) | 20 m²/g | 4 m²/g | 3 m²g |
| cumulated pore volume | 0.7 ml/g | 0.4 ml/g | 0.4 ml/g |
| Al content | 1.3% b.w. | 0.31% b.w. | <0.03% b.w. |
| Si content | 25% b.w. | 25% b.w. | 24% b.w. |
| $H_2PO_4$ content | 35% b.w. | 36% b.w. | 35% b.w. |
| ethene turnover at start of experiment | 5% | 5% | 6% |
| volume-time yield (ethanol) at start of experiment | 77.4 g/$l_{cat}$/hr | 76.4 g/$l_{cat}$/hr | 79.8 g/$l_{cat}$/hr |

What is claimed is:

1. A method of producing a phosphoric impregnated catalyst/catalyst carrier containing less than 0.3% by weight aluminum comprising impregnating a lattice-layer silicate with an acid, hydrothermally treating the acid-impregnated lattice-layer silicate at a temperature of between 160 and 300° C. and a partial water vapor pressure of between 4 and 80 $bar_{abs}$, and washing the hydrothermally treated, acid-impregnated, lattice-layer silicate with a wash solution selected from the group consisting of acidic solutions, basic solutions, and neutral solutions, wherein as part of the method, the lattice layer silicate is impregnated with phosphoric acid.

2. The process according to claim 1 wherein said neutral solution is water.

3. The process according to any one of claim 1 or 2 wherein said washing takes place at a temperature of between 20 and 100° C.

4. The process according to claim 3 wherein said washing takes place at a temperature of between 70 and 90° C.

5. The process according to any one of claim 1 or 2 wherein said washing solution comprises hydrochloric acid.

6. The process according to any one of claim 1 or 2 wherein the washed, hydrothermally treated, acid-impregnated, lattice-layer silicate is rinsed with water.

7. The process according to any one of claim 1 or 2 wherein said washing solution comprises water containing up to 30 parts of concentrated hydrochloric acid.

8. The process according to claim 6 wherein said rinsing is conducted until the rinsing water is neutral.

9. The process according to any one of claim 1 or 2 wherein said lattice-layer silicate is purified by burning off adhering organic carbon-containing compounds at a temperature of between 300 and 1000° C. prior to any of the steps set forth in claim 1.

10. The process according to any one of claim 1 or 2 wherein said hydrothermal treatment is conducted at a temperature of between 220 and 260° C. and a partial water vapor pressure of between 16 and 25 $bar_{abs}$.

* * * * *